(12) United States Patent
Cazzini (10) Patent No.: US 8,808,218 B2
(45) Date of Patent: Aug. 19, 2014

(54) NEEDLE PLACEMENT DETECTION AND SECURITY DEVICE AND METHOD

(75) Inventor: Karl H. Cazzini, Lindenhurst, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1020 days.

(21) Appl. No.: 12/696,707

(22) Filed: Jan. 29, 2010

(65) Prior Publication Data

US 2011/0190682 A1 Aug. 4, 2011

(51) Int. Cl.
*A61M 37/00* (2006.01)

(52) U.S. Cl.
USPC .......................................... 604/6.16

(58) Field of Classification Search
USPC ............. 604/4.301–6.16, 177, 198, 263, 264, 604/272, 309; 600/300, 309; 210/600, 634, 210/645, 646, 649–651
See application file for complete search history.

(56) References Cited

U.S. PATENT DOCUMENTS

| | | |
|---|---|---|
| 4,976,698 A | 12/1990 | Stokley |
| 5,036,859 A | 8/1991 | Brown |
| 5,137,033 A | 8/1992 | Norton |
| 5,266,928 A | 11/1993 | Johnson |
| 5,557,263 A | 9/1996 | Fisher et al. |
| 5,568,128 A | 10/1996 | Nair |
| 5,570,026 A | 10/1996 | Buffaloe, IV et al. |
| 5,790,036 A | 8/1998 | Fisher et al. |
| 5,796,345 A | 8/1998 | Leventis et al. |
| 5,868,723 A | 2/1999 | Al-Sabah |
| 5,931,802 A | 8/1999 | Yoshida et al. |
| 6,015,386 A | 1/2000 | Kensey et al. |
| 6,038,914 A | 3/2000 | Carr et al. |
| 6,090,048 A | 7/2000 | Hertz et al. |
| 6,113,577 A | 9/2000 | Hakky et al. |
| 6,189,388 B1 | 2/2001 | Cole et al. |
| 6,193,519 B1 | 2/2001 | Eggert et al. |
| 6,979,306 B2 | 12/2005 | Moll |
| 7,070,591 B2 | 7/2006 | Adams et al. |

(Continued)

FOREIGN PATENT DOCUMENTS

| | | |
|---|---|---|
| DE | 102006041265 B3 | 12/2007 |
| EP | 1401518 | 3/2004 |

(Continued)

OTHER PUBLICATIONS

International Search Report and Written Opinion for International Application No. PCT/US2010/062395 dated Mar. 29, 2011.

(Continued)

*Primary Examiner* — Philip R Wiest
(74) *Attorney, Agent, or Firm* — K&L Gates LLP (57) ABSTRACT

A blood access device includes (i) a conductive needle configured to pierce a patient's skin and gain access to a blood vessel; (ii) an insulative housing supporting a fluid communication junction between the needle and flexible tube; (iii) a conductor having a first end connected to the insulative housing and a second end extending from the insulative housing in a direction coextensive with the needle such that (a) when the needle has gained access to the blood vessel the patient's skin, the conductor is electrically insulated from the conductive needle and (b) if the needle is pulled so as to interrupt access with the blood vessel, the conductive needle and the conductor come into contact with each other.

21 Claims, 7 Drawing Sheets

(56) References Cited

U.S. PATENT DOCUMENTS

| | | |
|---|---|---|
| 7,147,615 B2 | 12/2006 | Wariar et al. |
| 7,176,344 B2 | 2/2007 | Gustafson et al. |
| 7,276,041 B2 | 10/2007 | Moll |
| 7,537,687 B2 | 5/2009 | Toyoda et al. |
| 7,641,612 B1 | 1/2010 | McCall |
| 7,670,289 B1 | 3/2010 | McCall |
| 8,094,041 B2 | 1/2012 | Wentland et al. |
| 2004/0116867 A1 | 6/2004 | Sternby |
| 2005/0003825 A1 | 1/2005 | Miyake |
| 2005/0010265 A1 | 1/2005 | Fassio et al. |
| 2005/0256451 A1 | 11/2005 | Adams et al. |
| 2007/0293748 A1 | 12/2007 | Engvall et al. |
| 2008/0065006 A1 | 3/2008 | Roger |
| 2008/0195060 A1 | 8/2008 | Roger et al. |
| 2009/0082647 A1* | 3/2009 | Busby .................... 600/309 |
| 2009/0118592 A1 | 5/2009 | Klitgaard |
| 2009/0145446 A1 | 6/2009 | DeDecker |
| 2009/0287182 A1* | 11/2009 | Bishop et al. ............ 604/509 |
| 2009/0322543 A1 | 12/2009 | Crnkovich et al. |
| 2010/0016809 A1* | 1/2010 | Grober et al. ............ 604/272 |
| 2010/0100026 A1 | 4/2010 | Morris |

FOREIGN PATENT DOCUMENTS

| | | |
|---|---|---|
| EP | 1736185 A2 | 12/2006 |
| EP | 1892734 | 2/2008 |
| WO | 96/25904 | 8/1996 |
| WO | 99/24145 | 5/1999 |
| WO | 9924145 A1 | 5/1999 |
| WO | 99/26686 | 6/1999 |
| WO | 99/29356 | 6/1999 |
| WO | 2006/001759 | 1/2006 |
| WO | 2009/024333 | 2/2009 |
| WO | 2009/075592 | 6/2009 |
| WO | 2009/109351 | 9/2009 |
| WO | 2009/112912 | 9/2009 |
| WO | 2009/112913 | 9/2009 |
| WO | 2010/040478 | 4/2010 |

OTHER PUBLICATIONS

U.S. Appl. No. 12/696,850, filed Aug. 4, 2011, Cazzini.

Written Opinion for International Application No. PCT/US2010/062396 dated Apr. 4, 2011.

Notification of Transmittal of the International Preliminary Report on Patentability for International Application No. PCT/US2010/062396 dated Jan. 30, 2012.

International Search Report and Written Opinion for International Application No. PCT/US2010/062395 dated Jul. 31, 2012.

\* cited by examiner

NEEDLE PLACEMENT DETECTION AND SECURITY DEVICE AND METHOD

BACKGROUND

The present disclosure relates to needle access disconnection detection.

It is especially important in instances in which a catheter enabled therapy is performed while the patient is sleeping or who otherwise may move in a manner likely to compromise catheter position and/or catheterization integrity to have an access disconnection detection system. Traditional means for attaching a catheter to a patient include the use of adhesive catheter securing devices, such as a Grip-Lok™ Universal Catheter Securement manufactured by Zefon International Inc. While a mechanical securement is beneficial, the device provides no recourse if the needle becomes dislodged despite the securement device.

Devices that sense when a needle dislodgement occurs are also available, such as a RedSense™ device manufactured by RedSense Medical, which alarms when an absorbent pad covering the catheterization site becomes saturated with blood flowing from a wound site upon inadvertent catheter withdrawal. Disadvantages of this device include its requirement of a relatively large amount of blood to activate the device, and the device's passive audible alarm, which may not be heard by patients with hearing impairment or subject to other environmental sound source. Also, the alarm is not fed back to the dialysis machine.

Other prior art access disconnection systems rely on current flowing through the patient's blood to indicate that a proper needle access exists. A drawback of these systems is that current must flow in many instances through high impedance or high resistance components, such as, a pump (membrane or peristaltic), a bubble trap, a valve or filter. These systems accordingly can succumb to noise, ground loops or loss of signal.

A more robust electrical access disconnection system, in particular for blood cleansing renal therapy treatments, such as hemodialysis, hemofiltration and hemodiafiltration, in which loss of a venous needle can lead to severe blood loss, is needed accordingly.

SUMMARY

The present disclosure sets forth multiple embodiments for a system and method for determining when a needle (referring collectively to a needle, catheter, cannula or other piercing member) inserted into a patient's blood vessel has come free or loose. Each embodiment utilizes the fact that when the needle is properly inserted into the patient's blood vessel, the patient's skin electrically insulates the distal end of the needle from the outside world. The embodiments set forth an apparatus having a conductor that (i) sits above the needle when the needle is inserted and (ii) resides outside the patient's skin so as not to make electrical contact with the distal end of the needle. When the needle becomes dislodged from the patient, the conductor comes into contact with the distal end of the needle and completes an electrical circuit. The completion of the electrical circuit can be used to control a medical fluid delivery machine function, such as, stop a blood pump and possibly additionally a dialysate pump, sound an alarm, or both.

In one embodiment, the proximal end of the needle is provided in an insulative housing. The insulative housing connects at its other end to a tube, such as a venous or arterial tube of an extracorporeal circuit. The insulative housing also houses the electrical conductor. The conductor can be hidden or retracted into the insulative housing before the needle is inserted into the patient's blood vessel. The patient then slides or rotates the conductor from the retracted position, into a deployed or activated or activated position on the outside of the patient's skin, above the inserted needle.

In one embodiment, the deployment of the conductor is done automatically such that the patient is not forced to remember to set the conductor. For example, the housing can be fitted with butterfly flanges that lay against the patient's skin and enable the patient to help secure the housing and needle by providing additional surface area by which to tape or otherwise secure the housing to the patient's body. The butterfly flanges can be provided in an initial folded-up position. A mechanism mechanically bridges the butterfly flanges and the conductor. When the patient folds the butterfly flanges down into place, the mechanism in turn rotates or slides the conductor into position overlying the patient's skin and the inserted needle.

In one embodiment, the electrical contact made between the needle and the conductor is a first electrical contact. A second electrical contact is made when the conductor is deployed or activated, e.g., via the deployment of the butterfly flanges. The second electrical contact is tied electrically with the dialysis machine such that the second contact needs to be made for a machine function to occur, e.g., for a blood (or possibly alternatively or additionally a dialysate) pump to operate. In this way, the machine will not be able to pump blood (and/or dialysate) unless the second contact is made, ensuring that the conductor is deployed or activated or activated before the patient's blood is pumped. The second electrical contact enables the medical fluid or dialysis machine and the first electrical contact disables the machine.

The conductor is one embodiment is pre-stressed, biased and/or spring-loaded and/or made of a superelastic material to contact the patient's skin. The conductor is wide enough to allow for lateral misalignment with the inserted needle. The conductor can also include a hook or other distal end configuration for securely engaging the needle if it is pulled accidentally from the patient's blood vessel. All of the above features of the conductor help to ensure that a good electrical contact is made with the needle upon dislodgment.

As discussed, the electrical contact between the machine and the conductor is tied in an embodiment to the machine. Electrical leads extend back to the dialysis machine, which includes a voltage source to power the circuit. In another embodiment the voltage source is localized at the access device, e.g., within the insulative housing. Here, the voltage source can be a battery, e.g., a rechargeable battery. The local voltage source also powers an emitter, such as a radio frequency, BlueTooth™, Zigbee™ or other type of wireless emitter. The dialysis machine is fitted with a corresponding receiver. The receiver receives a first signal from the emitter when the conductor is properly deployed or activated or activated. The receipt of the first signal enables a machine function, e.g., blood pump, to be operable. If the machine receiver receives a second signal from the emitter due to the conductor making electrical contact with a dislodged or partially dislodged needle, the dialysis machine enters an alarm state, stops the blood pump and takes any other desired action, such as closing arterial and venous blood line valves.

It is accordingly an advantage of the present disclosure to provide a blood access disconnection device that can enable and disable a dialysis machine, such as a hemodialysis machine.

It is another advantage of the present disclosure to provide a blood access disconnection device that does not require a significant reconfiguration of the dialysis machine.

It is a further advantage of the present disclosure to provide a blood access disconnection device that is fail safe.

It is yet another advantage of the present disclosure to provide a blood access disconnection device that is resettable.

Additional features and advantages are described herein, and will be apparent from the following Detailed Description and the figures.

DETAILED DESCRIPTION

Figure 1:
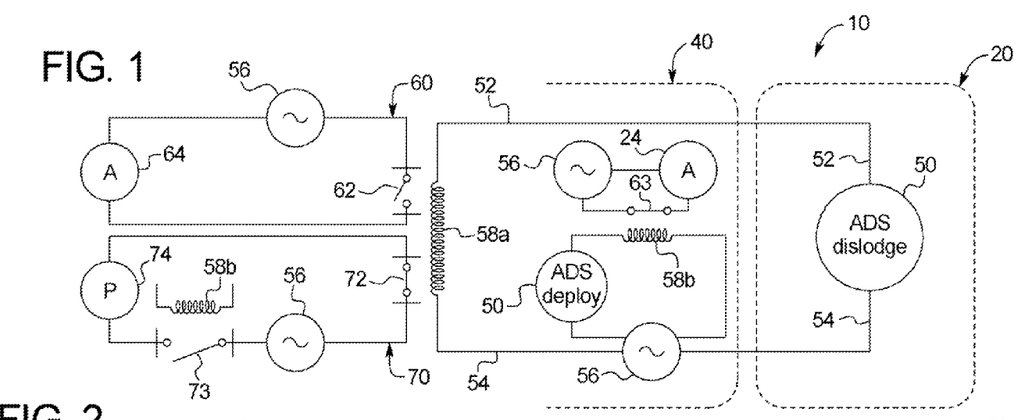
FIG. 1 is a schematic diagram of one electrical layout for the blood access disconnection device and system of the present disclosure.

Referring now to the drawings and in particular to FIG. 1, one embodiment of a blood access device and corresponding system and method is illustrated by system 10. System 10 includes a blood access device 20, which is generally shown in bordered phantom line. System 10 also includes a medical machine 40, such as a hemodialysis ("HD") machine, hemofiltration ("HF") machine, hemodialfiltration ("HDF") machine, continuous renal replacement therapy ("CRRT") machine, drug infusion pump or other type of medical device that involves the accessing of the patient's blood vessel with a needle, cannula, catheter or other type of blood vessel access member (which may be referred to herein collectively simply as a needle). In one preferred embodiment, medical machine 40 is an HD machine, and in particular a hemodialysis machine set forth in published U.S. Patent Publication 2009/0101549, the entire contents of which are incorporated herein by reference and relied upon.

Blood access device 20 includes an access disconnection apparatus 50, which is described in detail below beginning at FIGS. 3A and 3B. Access disconnection apparatus 50 communicates with conductors, wires or leads 52 and 54, which extend from blood access device 20 to medical fluid delivery machine 40. Conductors 52 and 54 can for example be printed circuit board traces or wires located on a printed circuit board ("PCB") of blood access device 20. PCB traces 52 and 54 can then communicate via a protected cable with medical fluid delivery machine 40.

In an alternative embodiment, conductors 52 and 54 extend along or within the medical delivery tubing that delivers a medical fluid from machine 40 to the patient at blood access device 20. In an HD, HDF or HF embodiment, there is a small section of tubing that extends from each of the arterial and venous needles inserted into the patient. Those small sections of tubing are then connected to arterial and venous lines running from the HD, HF or HDF machine 40, e.g., via standard lure lock connectors. It is contemplated to extend the wire through both the short tubings extending from the needles or catheters and the arterial and venous lines of machine 40. Various embodiments for extending a wire along the outside or within the wall of arterial and venous tubings are disclosed in U.S. patent application Ser. No. 12/360,503 (published as U.S. Publication No. 2009/0209916), filed Jan. 27, 2009, entitled "Sealant Applicator With Malleable Section", assigned to the assignee of the present disclosure, the entire contents of which are incorporated herein by reference. In any case, conductors 52 and 54 in an embodiment extend all the way to machine 40 of system 10.

In the illustrated embodiment, a voltage source 56 is provided along one of conductors 52 and 54 to supply power to blood access device 20 from within machine 40. Voltage source 56 can be an AC or DC voltage source as desired. Conductors 52 and 54 terminate at a logic coil 58. Coil 58a can be the coil of an electromechanical relay or of a solid-state relay, such as one provided within a programmable logic controller ("PLC"), which is used commonly with electrically controlled devices for the control of electrical logic.

Relay coil 58a in the illustrated embodiment is configured to energize or change the state of a normally closed electrical contact 72 associated with a pump circuit 70, and a normally open contact 62 associated with an alarm circuit 60. Each of pump circuit 70 and alarm circuit 60 is powered by a power supply or voltage source 56, which can be the same or different voltage source 56 used in the circuit of conductors 52 and 54. It should be appreciated that circuits 60 and 70 have been simplified and may contain other electrical components known to those skilled in the art.

In operation, when the patient inserts the needle into the patient's blood vessel and deploys access disconnection apparatus $50_{dislodge}$ as shown below, current does not flow through conductors 52 and 54 and does not energize logic coil 58a. Thus, pump 74 is allowed to function selectively and alarm 64 is not operated or alarmed. Upon an access disconnection event causing a contact closure at access disconnection apparatus $50_{dislodge}$, logic coil 58a is energized via conductors 52 and 54 and voltage supply 56, which in turn causes contacts 62 and 72 to change state. In circuit 60, normally open contact 62 closes, such that voltage supply 56 can supply power to alarm 64, causing the alarm to operate. Likewise, the energizing of logic coil 58a causes normally closed contact 72 to open, such that current no longer is supplied from voltage source 56 to pump 74.

Alarm 64 can be a visual alarm, audio alarm or audiovisual alarm. It is contemplated for to provide a second, different contact 73 for the deployment of access disconnection apparatus $50_{deploy}$, which closes normally open contact 73 to enable pump 74. Prior to such deployment, an additional normally closed contact 63 to a second alarm 24 is not energized, causing second alarm 24 to be operated. Second alarm 24 may simply be a light that is lit prior to the patient deploying access disconnection apparatus $50_{deploy}$, prompting the patient to deploy access disconnection apparatus $50_{deploy}$. After such deployment, a second coil 58b becomes energized, opens the normally closed contact 63 and causes the light of the second alarm 24 to switch off. It is contemplated to make access disconnection alarm 64 a more intrusive audio or audio-visual alarm, such that if one of the needles comes loose from the patient, coil 58a becomes energized, contact 62 closes and voltage supply 56 powers the more intrusive alarm 62, which alerts the patient (who may for example be sleeping) to promptly correct the access disconnection situation.

As illustrated, second coil 58b ensuring deployment of access disconnection apparatus 50, also closes a second normally open contact 73 provided in pump circuitry 70, which enables pump 74 to be operated. The corollary to such condition is that if the patient does not deploy access disconnection apparatus 50, second coil 58b does not become energized, such that the second normally open contact 73 provided in pump circuitry 70 does not close, and pump 74 cannot be operated.

Pump circuitry 70 may have additional override circuitry (not illustrated) that allows pump 74 to be operated even though coil 58a has been energized and/or coil 58b has not been energized. For purposes of the present disclosure, however, circuit 70 when coil 58a is in an un-energized state, maintains contact 72 in its normally closed condition, such that voltage supply 56 can supply power to pump 74. When access disconnection apparatus 50 is in a blood vessel properly accessed condition, coil 58a is not energized, and normally open contact 62 remains in its un-energized or open state, which prevents alarm 64 from sounding or lighting. When coil 58a is not energized, normally closed contact 72 remains in its energized or closed state, which enables voltage source 56 to selectively power pump 74 (assuming deployment contact 73 has been closed). Thereafter, if a needle disconnection event occurs, coil 58a becomes energized and contact 72 switches to its open state, and causes pump 74 to stop.

While system 10 is shown having both circuitry 60 and circuitry 70, it may be desirable in certain instances to provide only one of alarm circuitry 60 or pump circuitry 70.

Figure 2:
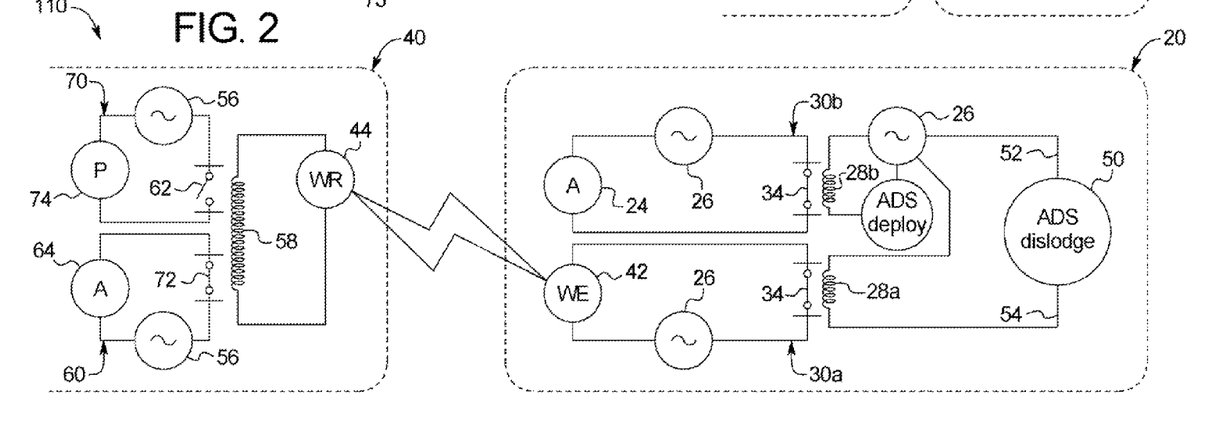
FIG. 2 is schematic diagram of another electrical layout for the blood access disconnection device and system of the present disclosure.

Referring now to FIG. 2, an alternative wireless system 110 is illustrated. System 110 includes many of the same components described above for system 10, including machine voltage source 56 and alarm and pump circuits 60 and 70 respectively, which operate as described above for system 10, including any additional desirable electrical components common to those of skill in the art, which are not shown here for ease of illustration. Also, just like with system 10, normally open contact 62 and normally closed contact 72 are energized via logic coil 58, located within machine 40. Blood access device 20 includes access disconnection apparatus 50 and conductors 52 and 54 as described above for system 10.

In system 110, however, blood access device 20 is not powered by machine 40 and instead includes its own separate voltage supply 26, which can be a single voltage supply for all components of blood access device 20 or can be multiple, e.g., regulated, voltage supplies for different components of blood access device 20. In an embodiment, voltage supply 26 is a rechargeable battery supply, for which it is contemplated to configure alarm circuitry 30b to sound an alarm 24 whenever the voltage level stored in supply 26 falls below a preset level.

Blood access device 20 includes pump energizing and alarm output circuits 30a and 30b, respectively, which operate in a similar manner to alarm and pump output circuits 60 and 70 described above for system 10. In particular, when the needle is accessing the patient's blood vessel, no current flows from voltage source 26 through coil 28a, such that coil 28a remains unenergized. Consequently, normally closed contact 34 of pump energize or wireless emitter circuit 30a remains in its unenergized state (ADS 50$_{dislodge}$).

System 110 can again form a dual stage alarm, such that local alarm 24 merely shines a light to inform the patient prior to deployment of access disconnection apparatus 20 and becomes deactivated upon deployment of access disconnection apparatus 20 (ADS 50$_{dislodge}$), via a second coil 28b that is energized upon such deployment to open a normally closed contact 34 of circuit 30b. Machine alarm 64, which is sounded upon a needles access disconnection, provides a more invasive alarm.

Under ADS 50$_{dislodge}$, in the unenergized (needle accessed) state, power supply 26 does supply power to a wireless emitter 42 coupled to wireless emitter circuit 30a, such that a signal is sent wirelessly to a wireless receiver 44 located in an electrical circuit with coil 58 within machine 40. When a needle dislodgment event occurs to close a switch at access disconnection apparatus 20 shown below, current is enabled to flow through coil 28a, causing contact 34 of circuit 30a to switch to its energized state. Wireless emitter circuit 30a becomes energized such that wireless emitter 42 no longer sends a wireless signal to wireless receiver 44.

Upon receiving wireless signal at receiver 44 (when vessel access is properly made), machine coil 58 becomes energized (i) closing contact 62 and enabling pump 74 to be selectively operated, and (ii) opening contact 72 to cause alarm 64 to become disabled. In the event that vessel access is not properly made, such that there is no signal at wireless receiver 44, machine coil 58 becomes unenergized and prevents pump 74 from being operated and causes invasive alarm 64 to sound and/or become lighted. Wireless emitter 42 and wireless receiver 44 communicate in an embodiment via a known wireless communication protocol, such as Bluetooth™ Zigbee™, or other protocol, e.g., one based on IEEE 802.

The access disconnection apparatuses shown below are for a single one of the arterial or venous blood needles. It may be that only the venous needle is equipped with one of the access disconnection apparatuses. It should be appreciated that both venous and arterial needles may be equipped with one of the access disconnection apparatuses, in which certain of the electronics of systems 10 and 110 are repeated, which should be apparent to those of skill in the art, but wherein the duplicated electronics are structured to operate with the same blood pump 74 and the same alarm 64, such that multiple blood pumps and alarms are not required unless desired.

Figure 3A:
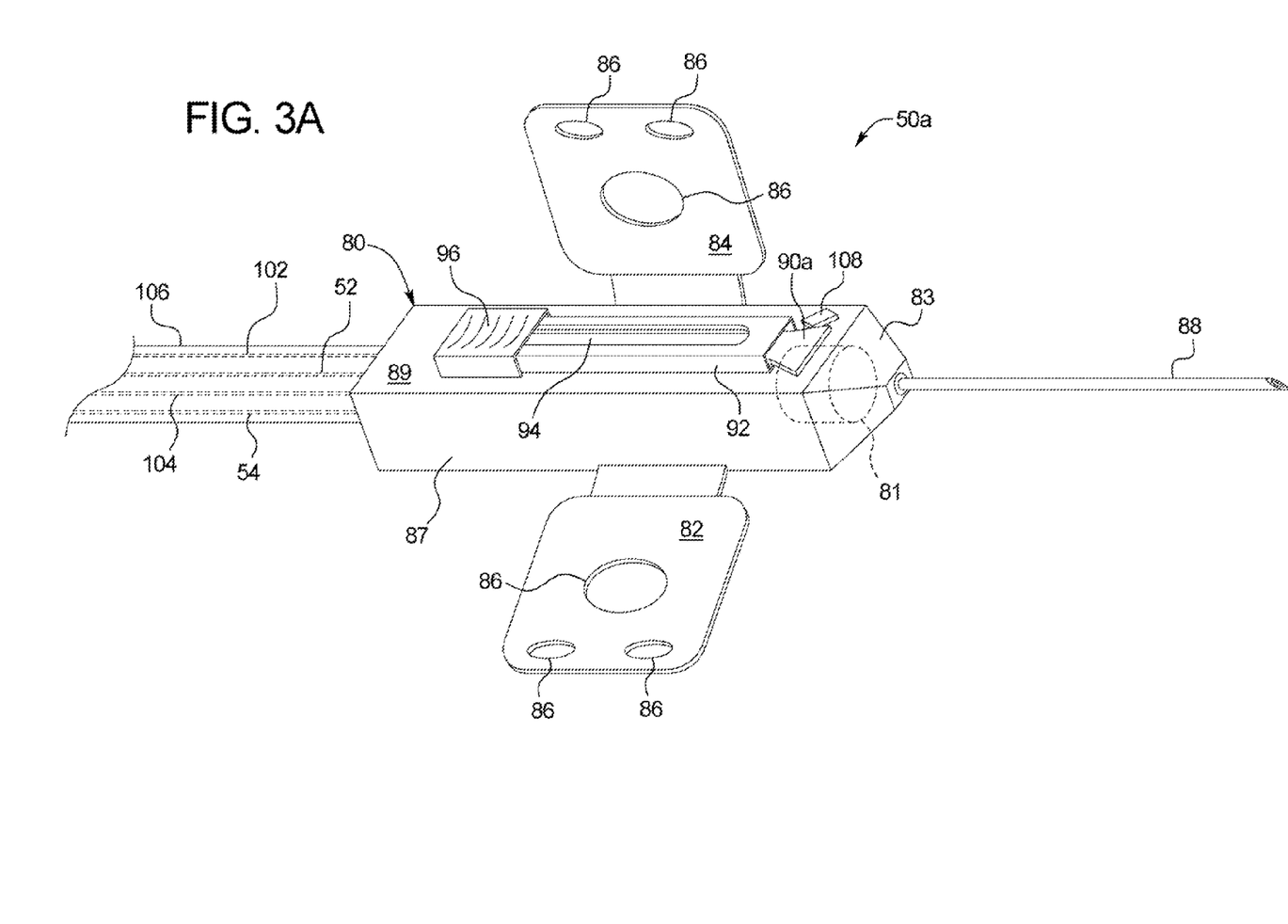
FIG. 3A is an elevation view of one embodiment of the blood access disconnection device of the present disclosure in a retracted condition.
Figure 3B:
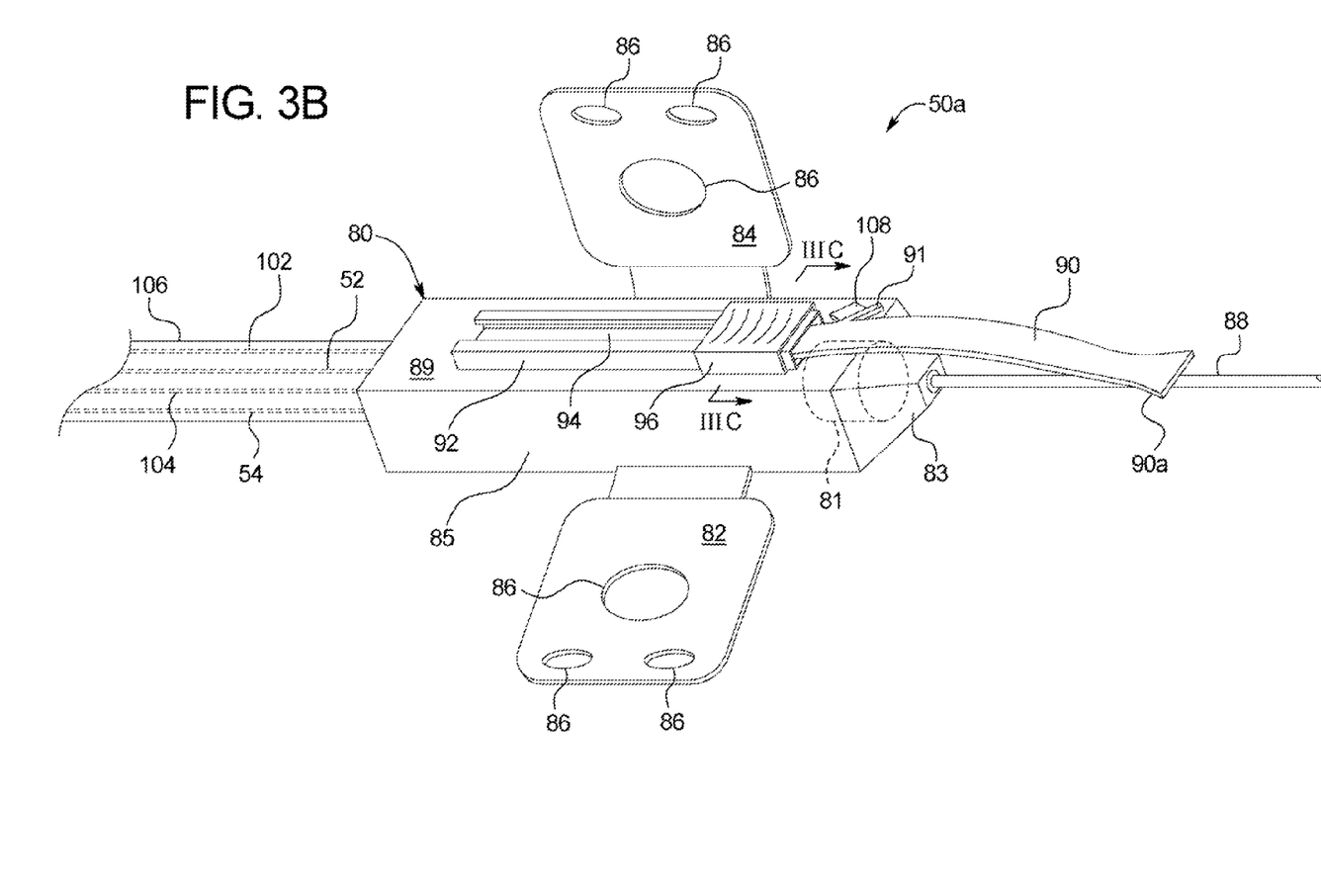
FIG. 3B is an elevation view of the embodiment of FIG. 3A in a deployed or activated or activated condition.
Figure 3C:
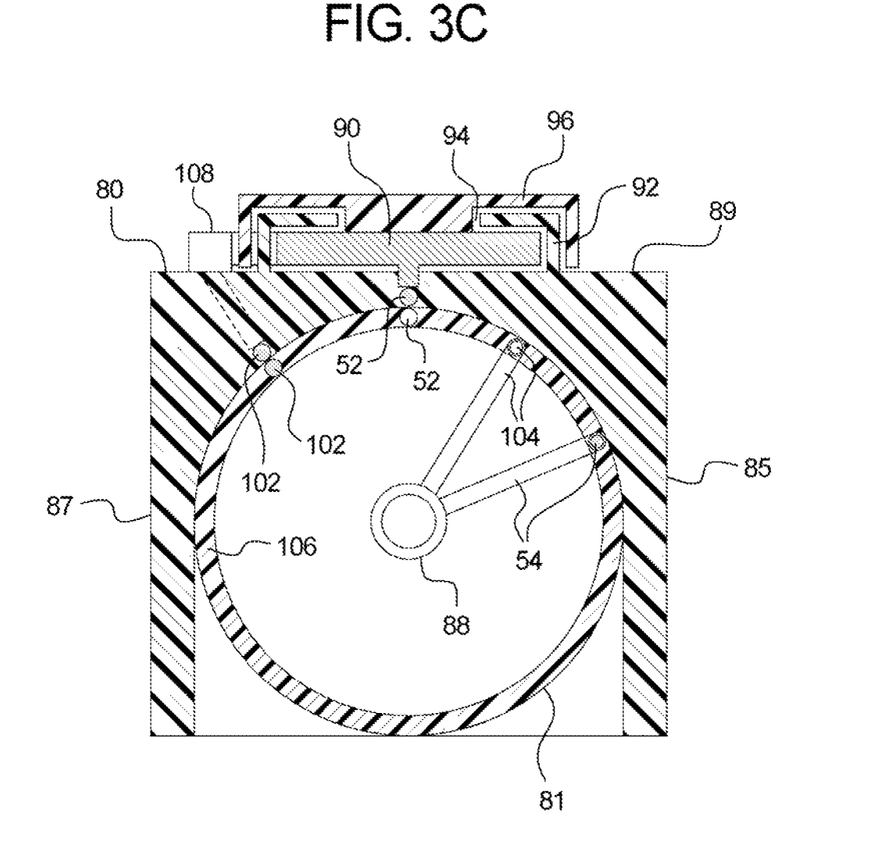
FIG. 3C is a sectioned elevation view taken along line IIIC-IIIC of FIG. 3B.

Referring now to FIGS. 3A to 3C, one embodiment of a access disconnection apparatus is illustrated by apparatus 50a (device 50 referring collectively to apparatuses 50a, 50b, 50n, etc.). Apparatus 50a includes an insulative housing 80, which can be made of a medical grade polymer material. Housing 80 defines a bore 81 that sealingly accepts tube 106. Bore 81 ends at a nozzle section 83 of housing 80. Nozzle section 83 narrows in cross-section to sealingly accept needle 88, which extends into nozzle section 83 to communicate fluidly with tube 106. The four-sided section of housing 80 defining bore 81 transitions in one embodiment to a three-sided U-shaped section having flange walls 85 and 87 that extend down from the top surface 89 of housing 80 so as to fit snugly about tube 106.

Butterfly flanges 82 and 84 extend from the bottoms of flange walls 85 and 87, respectively, of housing 80 and provide apertures 86. Butterfly flanges 82 and 84 help with the insertion of cannula or needle 88 and also enable housing 80 to be stabilized once insertion into patient blood vessel has been made.

A retractable conductor 90 is fitted within a slotted guide 92. Slotted guide 92 in an embodiment is formed integrally, e.g., molded to the top surface 89 of housing 80. Guide 92 defines an elongated slot 94, which allows a locking thumb/finger slide 96 to be moved along elongated slot 94, which in turn moves conductor 90 from a retracted or inactivated position shown in FIG. 3A to a deployed or activated or activated position shown in FIG. 3B. In an embodiment, conductive lead 52 is connected electrically to retractable conductor 90, while conductive lead 54 is connected electrically to needle or cannula 88 of access disconnection apparatus 50a.

A second set of conductive leads 102 and 104 is provided to ensure that conductor 90 is deployed or activated into an operating position prior to allowing a machine function, such as the operation of a blood and/or dialysis pump to occur. Conductive lead 102 extends to a conductive pad 108 located in housing 80. Conductive lead 104, like conductive lead 54, extends to needle or cannula 88. As illustrated, each conductive lead 52, 54, 102 and 104 can be located within the wall of medical fluid tubing 106 in a manner described above. In another example, conductive leads 52, 54, 102 and 104 can be conductive tape or ink placed on the outer wall of tubing 106, which can be covered with an insulating layer, such as an insulative tape. Tubing 106 is in one embodiment a small section of tubing that extends from housing 80 a short distance (e.g., ten inches or twenty-five centimeters), and which connects to arterial or venous lines extending of the extracorporeal circuit of machine 30.

As discussed, conductive lead 52 either resides along the outside of tube 106, or resides within the wall of tube 106 and extends around the sealed end of tube 106 and along the outside of tube 106, and in either case provides a track along the outside of tube 106, so as to form a conductive slip-engagement with a conductive tab 93 shown in FIG. 3C extending from conductor 90 downwardly through the top wall 89 of housing 80. In this manner, conductor 90 and conductive lead 52 remain in electrical contact regardless of the sliding position of thumb/finger slide 96 and corresponding conductor 90.

Similarly, conductive lead 102 either resides along the outside of tube 106, or resides within the wall of tube 106 and extends around the sealed end of tube 106 and along the outside of tube 106, and in either case provides a track along the outside of tube 106, so as to form a permanent conductive engagement with a conductive tab 108 shown in FIG. 3B extending through the top wall 89 of housing 80.

Conductive leads 54 and 104 are connected electrically to needle or cannula 88 of access disconnection apparatus 50a. Conductive leads 54 and 154 extend along the outer surface or tube 106, or within wall of tube 106, to the sealed and of tube 106 and then extend inwards toward the radial center of tube 106, at which point conductive leads 54 and 104 make electrical contact with needle or cannula 88, which extends into nozzle 83 of housing 80 and terminates at approximately the same horizontal or longitudinal point within housing 80 as does tube 106.

FIG. 3A shows that in the retracted position, conductor 90 does not make an electrical contact with conductive pad 108. However, in FIG. 3B, when conductor 90 is deployed or activated, a conductive spring flange 91 extending from conductor 90 comes into electrical contact with conductive pad 108, which communicates electrically with conductive lead 102 to complete a "conductor deployed or activated circuit". Spring flange 91 folds into guide 92 when conductor 90 is retracted and springs open to engage conductive pad 108 when conductor 90 is deployed or activated.

When "conductor deployed or activated circuit" is completed, the dialysis machine is enabled for operation of one or more machine function, such as, the running of a blood pump and/or dialysate pump. Also, as discussed above, when "conductor deployed or activated circuit" is completed, the mild alarm or reminder 64 of system 10 and mild alarm or reminder 24 of system 110 is disabled. The communication of the completion of the "conductor deployed or activated circuit" can accordingly be done according to the wired system 10 of FIG. 1 or wireless 110 of FIG. 2, as discussed above.

In FIG. 3B, deployed or activated or activated conductor 90 is shown making electrical contact with needle or cannula 88. In particular, a tip 90a of conductor 90 can be biased or bent so as to be predisposed to contact needle or cannula 88. Tip 90a can be widened as needed to account for a misalignment between conductor 90 and needle or cannula 88. As seen in FIG. 3A, tip 90a in one embodiment resides just outside channel guide 92 when conductor 90 is in the retracted position, so that guide 92 does not have be wide enough to accommodate the enlarged tip 90a.

In normal operation, when needle or cannula 88 is inserted into the patient's blood vessel, the patient's skin acts as an electrical insulator between conductor 90 and needle or cannula 88. Upon an access disconnection event, needle or cannula 88 is pulled out from the patient's blood vessel, such that biased conductor 90 makes electrical contact at tip 90a with needle or cannula 88. System 10 or 110 is then caused to open the pump circuit and stop the one or more machine pump and sound and/or show an alarm, as discussed above in connection with systems 10 and 110.

Figure 4:
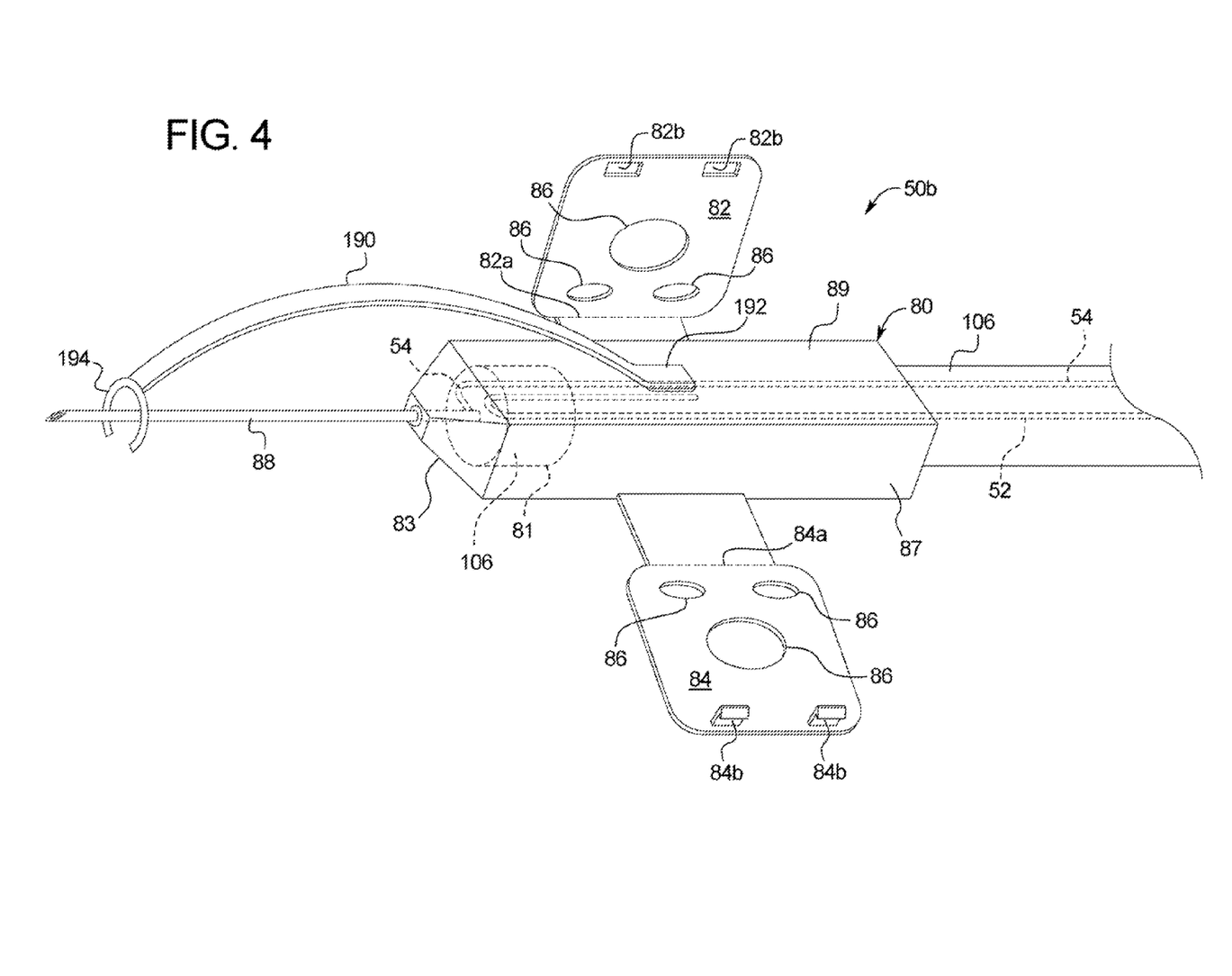
FIG. 4 is an elevation view of a second embodiment of the blood access disconnection device of the present disclosure.

FIG. 4 illustrates an alternative access disconnection apparatus 50b. Apparatus 50b also includes an insulative housing 80, which can be made of a medical grade polymer material. Housing 80, like above defines a bore 81 that sealingly accepts tube 106. Bore 81 ends at nozzle section 83 of housing 80. Nozzle section 83 narrows in cross-section to sealingly accept needle 88, which extends into nozzle section 83 to communicate fluidly with tube 106. The four-sided section of housing 80 defining bore 81 transitions again, in one embodiment, to a three-sided U-shaped section having flange walls 85 and 87 that extend down from the top surface 89 of housing 80 so as to fit snugly about tube 106. Butterfly flanges 82 and 84 extend from the bottoms of flange walls 85 and 87, respectively, of housing 80 and provide apertures 86.

Here, alternative conductor 190 is made of a superelastic (also called psuedoelastic or shape memory) material, such as Nitinol (a nickel titanium alloy). Such material which can have both shape memory and superelastic forms. In this application, the material would be shaped according to methods known to those in the art so that conductor 190 retains its trained shape at all times. That is, conductor 190 is pre-bent, not bent into shape by the user, and if the user straightens conductor 190, the conductor will spring back into its shape.

There are other polymer materials which, while not exhibiting "superelasticity" as Nitinol can, exhibit useful reversible strain, making them suitable for conductor 190. Such polymer materials would then support an integrated or attached conductive tab at the end of the conductor a material (not illustrated). There may be economic and/or manufacturability advantages to using a shape memory polymer member supporting a conductor. However Nitinol, in one preferred embodiment, has the advantage of fulfilling both the "retention" and "conductor" functions simultaneously in a single element.

Superelastic conductor 190 is folded backwards and in a non-deployed or inactivated position when butterfly flanges 82 and 84 are initially folded up along fold lines 82a and 84a of connecting flanges 82 and 84, respectively, to housing 80. Flanges 82 and 84 in the illustrated embodiment include mating locking mechanisms 82b and 84b that hold (i) flanges 82 and 84 together and (ii) superelastic conductor 190 in the folded-back position until flanges 82 and 84 are pulled apart and folded down onto the patient's skin.

Conductor 190 at its base 192 is welded to top wall 89 of housing 80 so as to predispose or bias conductor 190 towards needle or cannula 88. When flanges 82 and 84 are pulled apart and folded down onto the patient's skin, conductor 190 unfolds from its un-preset condition over to its preset condition, which is above needle or cannula 88. When the patient has inserted needle or cannula 88 into the patient's skin, the skin separates conductor 190 electrically from needle or cannula 88. In the illustrated embodiment, retractable conductor 190 extends to an end 194 of conductor 190 that is configured to mate with and maintain electrical communication with needle or cannula 88.

Access disconnection apparatus 50b also uses conductive leads 52 and 54. Conductive lead 52 again either resides along the outside of tube 106, or resides within the wall of tube 106 extending around the sealed end of tube 106 and along the outside of tube 106, and in either case provides a conductive track along the outside of tube 106, so as to form a conductive engagement with a conductive tab (like tab 93 of FIG. 3C) extending from welded end 192 of conductor 190 downwardly through the top wall 89 of housing 80.

Conductive lead 54 is again connected electrically to needle or cannula 88 of access disconnection apparatus 50b. Conductive lead 54 (leads 52 and 54 of access disconnection apparatus 50b can be of any of the types discussed above for access disconnection apparatus 50a) extends along the outer surface or tube 106, or within wall of tube 106, to the sealed and of tube 106 and then extends inwards towards the radial center of tube 106. At the center of tube 106, lead 54 makes electrical contact with needle or cannula 88, which extends into nozzle 83 of housing 80 and terminates at approximately the same horizontal or longitudinal point within housing 80 as does tube 106.

Because conductor 190 is auto-deploying upon the attachment of flanges 82 and 84 to the patient, it may be found that the second set of conductive leads 102 and 104 and associated electronics, provided to ensure that conductor 90 of access disconnection apparatus 50b is deployed or activated into an operating position, may not be needed. However, second leads 102 and 104 (FIGS. 3A to 3C) may be provided if desired. For example, conductive lead 102 (FIGS. 3A to 3C) could extend to a conductive pad located on housing 80, while conductive lead 104 (FIGS. 3A to 3C), like conductive lead 54, extends to needle or cannula 88.

Lead 102 (FIGS. 3A to 3C) would again complete a "conductor deployed or activated circuit". When the "conductor deployed or activated circuit" has been made or completed, the dialysis or medical fluid machine would be enabled for operation of one or more machine function, such as, the running of a blood pump and/or dialysate pump. Also, when the "conductor deployed or activated circuit" has been completed, mild alarm or reminder 64 of system 10 and mild alarm or reminder 24 of system 110 would be disabled. The communication of the completion "conductor deployed or activated circuit" can again be done according to the wired system 10 of FIG. 1 or wireless 110 of FIG. 2, as discussed above.

In FIG. 4, deployed or activated conductor 190 is shown making electrical contact with needle or cannula 88. Tip 194 of conductor 190 can again be widened as needed to account for a misalignment between conductor 190 and needle or cannula 88. In normal operation, when needle or cannula 88 is inserted into the patient's blood vessel, the patient's skin acts as an electrical insulator between conductor 190 and needle or cannula 88. Upon an access disconnection event, needle or cannula 88 is pulled out from the patient's blood vessel, such that biased conductor 190 makes electrical contact with needle or cannula 88, system 10 or 110 is caused to open the pump circuit and stop the one or more machine pump and in turn sound and/or display an alarm, as discussed above in connection with systems 10 and 110.

Figure 5:
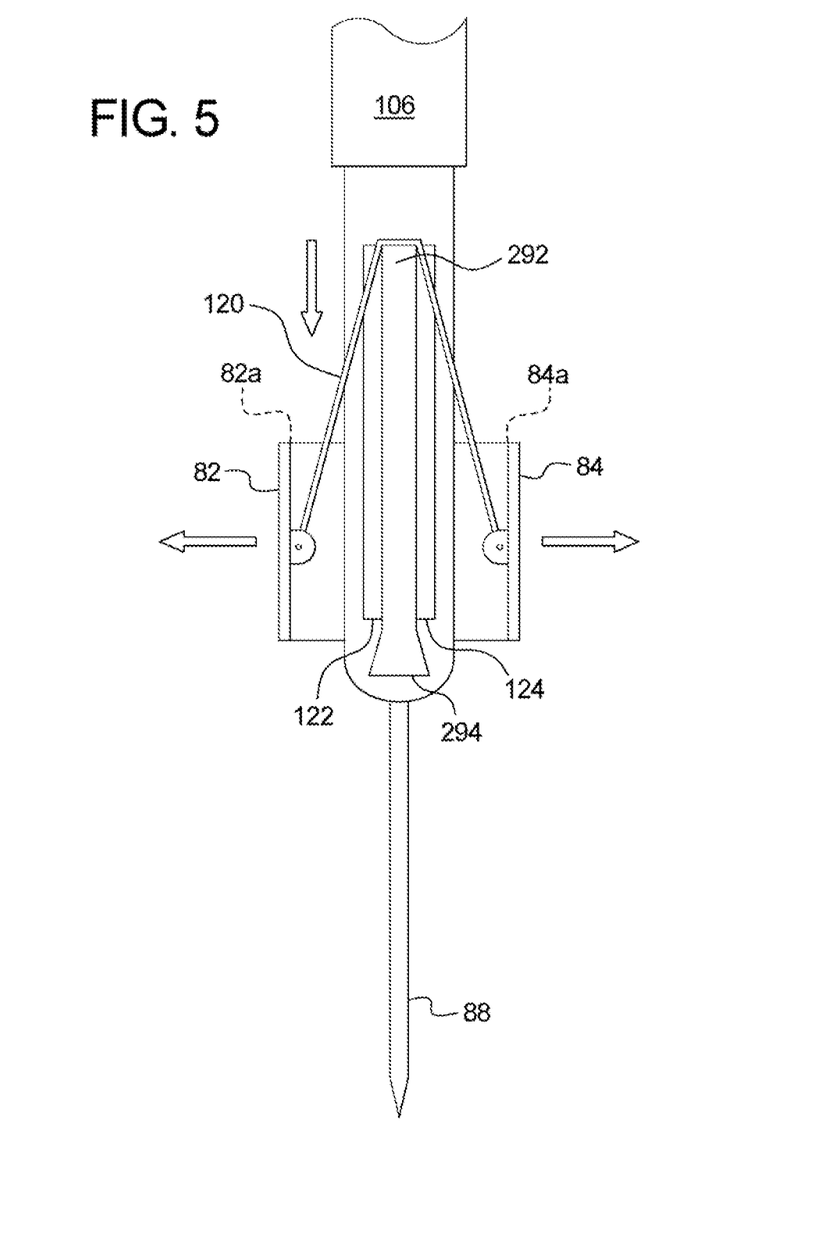
FIG. 5 is a top pan view a third embodiment of the blood access disconnection device of the present disclosure.

Referring now to FIG. 5, access disconnection apparatus 50c illustrated another embodiment of the present disclosure. Here, the attachment or rotating of flanges 82 and 84 down along fold lines 82a and 82b to the patient causes a chord or wire 120 to slide conductor 290 into position over needle 88. In particular, chord or wire 120 can be attached to a proximal end 292 of conductor 290 and reside elevationally above track guides 122 and 124 defining a track or groove in which conductor 290 slides. When flanges 82 and 84 are folded down along fold lines 82a and 82b onto the skin of patient 100, chord or wire 120 is pulled and in turn pushes conductor 290 at proximal end 292 slidingly within track guides 122 and 124, such that distal end 294 of conductor 290 resides at a desired location above needle 88. Distal end 294, like before, can be biased or pre-stressed so as to extend towards needle 88 (into the page) to ensure electrical contact with needle 88 if blood vessel access is impaired. Conductor 290 can be made of a superelastic material or of any of the materials described herein.

Figure 6:
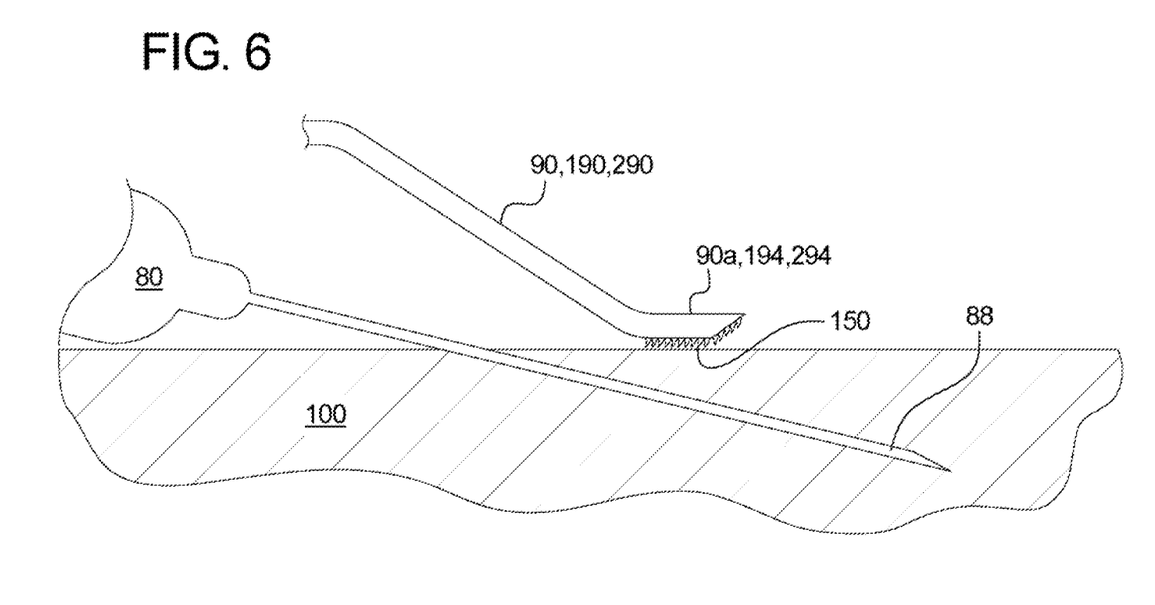
FIG. 6 is a side elevation view illustrating how the patient's skin electrically isolates the needle from the conductor when the needle is inserted properly and various embodiments for structuring the distal end of the conductor to help maintain electrical connection with the needle if an access disconnection event has occurred.

FIG. 6 illustrates that distal ends 90a, 194 and 294 of conductors 90, 190 and 290, respectively, can define or include a textured, micro-machined, or conductive adhesive surface 150, which helps to stabilize distal end 90a, 94 and 294 while residing along the skin of patient 100. If needle 88 is withdrawn from the blood vessel of patient 100, micromachined, textured or conductive adhesive surface 150 will help maintain a connection between conductor 90, 190 and 290 and needle 88.

Aspects of the subject matter described herein may be useful alone or in combination one or more other aspect described herein. Without limiting the foregoing description, in a first aspect of the present disclosure, a blood access device includes: a conductive needle configured to pierce a patient's skin and gain access to a blood vessel; an insulative housing supporting a fluid communication junction between the needle and flexible tube; a conductor having a first end connected to the insulative housing and a second end extending from the insulative housing in a direction coextensive with the needle such that (i) when the needle has gained access to the blood vessel the patient's skin, the conductor is electrically insulated from the conductive needle and (ii) if the needle is pulled so as to interrupt access with the blood vessel, the conductive needle and the conductor come into contact with each other.

In accordance with a second aspect of the present disclosure, which may be used in combination with the first aspect, the blood access device includes first and second leads extending from the conductive needle and the conductor, respectively, wherein a dialysis machine can interface electrically with the first and second leads to ensure that the needle has access to the blood vessel while performing a dialysis machine function.

In accordance with a third aspect of the present disclosure, which may be used in combination with any one or more of the preceding aspects, the blood access device includes first and second leads extending from the conductive needle and the conductor, respectively, a voltage source and a signal emitter in electrical communication with the first and second leads.

In accordance with a fourth aspect of the present disclosure, which may be used in combination with the third aspect, the blood access device includes a signal receiver connected operably to a dialysis machine, the signal receiver receiving a signal or a change in signal from the signal emitter when the needle access to the blood vessel has been interrupted.

In accordance with a fifth aspect of the present disclosure, which may be used in combination with any one or more of the preceding aspects, the blood access device includes first and second leads extending from the conductive needle and the conductor, respectively, and which includes an alarming device in electrical communication with the first and second leads, the alarming device providing an alarm when the conductive needle comes into contact with the conductor.

In accordance with a sixth aspect of the present disclosure, which may be used in combination with the fifth aspect, the blood access device includes a voltage source in electrical communication with the first and second leads.

In accordance with a seventh aspect of the present disclosure, which may be used in combination with any one or more of the preceding aspects, the conductor is moveably connected to the insulative housing, the second end adjacent to the insulative housing when the conductor is in an inactivated position, the second end extending from the insulative housing when the conductor is in an activated position.

In accordance with an eighth aspect of the present disclosure, which may be used in combination with any one or more of the preceding aspects, the conductor is slideably or rotatably connected to the insulative housing.

In accordance with a ninth aspect of the present disclosure, which may be used in combination with any one or more of the preceding aspects, the conductor includes a first electrode, the insulative housing including a second electrode, the first and second electrodes coming into contact with each other when the conductor is in the activated position.

In accordance with a tenth aspect of the present disclosure, which may be used in combination with the ninth aspect, the blood access device includes first and second leads extending from the first and second electrodes, respectively, wherein a dialysis machine can interface electrically with the first and second leads to ensure that the needle has gained access to the blood vessel before performing a dialysis machine function.

In accordance with an eleventh aspect of the present disclosure, which may be used in combination with the ninth aspect, the blood access device includes first and second leads extending from the first and second electrodes, respectively, a voltage source and a signal emitter in electrical communication with the first and second leads.

In accordance with a twelfth aspect of the present disclosure, which may be used in combination with the eleventh aspect, the blood access device includes a signal receiver connected operably to a dialysis machine, the signal receiver receiving a signal or a change in signal from the signal emitter when the needle has gained access to the blood vessel, the signal needed for the dialysis machine to perform a function.

In accordance with a thirteenth aspect of the present disclosure, which may be used in combination with any one or more of the preceding aspects, the conductor is at least one of: (i) biased to contact the conductive needle; and (ii) wide enough to account for a misalignment between the conductor and the conductive needle.

In accordance with a fourteenth aspect of the present disclosure, which may be used in combination with any one or more of the preceding aspects, the blood access device is configured to automatically move the conductor to the activated position upon the patient gaining access to the blood vessel.

In accordance with a fifteenth aspect of the present disclosure, which may be used in combination with any one or more of the preceding aspects, the insulative housing includes first and second mounting flanges that rotate into a position to be secured to the patient's arm, and which includes a mechanism that uses the rotation of at least one of the first and second mounting flanges to automatically move the conductor to the activated position.

In accordance with a sixteenth aspect of the present disclosure, which may be used in combination with any one or more of the preceding aspects, a blood access device includes: a conductive needle configured to gain access to a patient's blood vessel; first and second leads, the first lead in electrical communication with the conductive needle; and a conductor in electrical communication with the second lead, the conductor extending in a same direction as the needle such that (i) when the needle has gained access to the blood vessel, the conductive needle is electrically insulated from the conductor and (ii) if the need is pulled so as to interrupt access with the blood vessel, the conductive needle and the conductor come into contact with each other.

In accordance with a seventeenth aspect of the present disclosure, which may be used in combination with any one or more of the preceding aspects and aspect sixteen, the first and second leads extend to one of: (i) a dialysis machine and (ii) an alarming device.

In accordance with an eighteenth aspect of the present disclosure, which may be used in combination with any one or more of the preceding aspects and aspect sixteen, the conductor is configured to be moved from an inactivated position to an activated position, the conductor in the activated position located such that (i) when the needle has gained access to the blood vessel, the conductive needle is electrically insulated from the conductor and (ii) if the needle is pulled so as to interrupt access with the blood vessel, the conductive needle and the conductor come into contact with each other.

In accordance with a nineteenth aspect of the present disclosure, which may be used in combination with the eighteenth aspect and aspect sixteen, the blood access device is configured to make an electrical contact upon reaching the activated position, the electrical contact usable to enable a dialysis machine function.

In accordance with a twentieth aspect of the present disclosure, which may be used in combination with any one or more of the preceding aspects and aspect sixteen, the conductor is connected to a housing, the housing constructed and arranged to aid the needle in gaining access to the patient's blood vessel.

In accordance with a twenty-first aspect of the present disclosure, which may be used in combination with any one or more of the preceding aspects and aspect sixteen, the conductor is made of a superelastic material preset so that the conductor extends in a same direction as the needle.

In accordance with a twenty-second aspect of the present disclosure, which may be used in combination with any one or more of the preceding aspects, a blood access method includes: using a patient's skin as an electrical insulator such that an electrical contact is not made when access to a patient's blood vessel exists; and making the electrical contact when access to the patient's blood vessel is compromised due to a movement of a conductive needle previously inserted into the blood vessel such that the patient's skin no longer electrically insulates the needle from a separate conductor.

In accordance with a twenty-third aspect of the present disclosure and aspect, which may be used in combination with any one or more of the preceding aspects and aspect twenty-two, the blood access method further includes locating the conductor so that it lies outside the patient's skin above the conductive needle.

In accordance with a twenty-fourth aspect of the present disclosure, any of the structure and functionality illustrated and described in connection with FIG. 1 may be used in combination with any one or more of the preceding aspects.

In accordance with a twenty-fifth aspect of the present disclosure, any of the structure and functionality illustrated and described in connection with FIG. 2 may be used in combination with any one or more of the preceding aspects.

In accordance with a twenty-sixth aspect of the present disclosure, any of the structure and functionality illustrated and described in connection with FIG. 3A may be used in combination with any one or more of the preceding aspects.

In accordance with a twenty-seventh aspect of the present disclosure, any of the structure and functionality illustrated and described in connection with FIG. 3B may be used in combination with any one or more of the preceding aspects.

In accordance with a twenty-eighth aspect of the present disclosure, any of the structure and functionality illustrated and described in connection with FIG. 3C may be used in combination with any one or more of the preceding aspects.

In accordance with a twenty-ninth aspect of the present disclosure, any of the structure and functionality illustrated and described in connection with FIG. 4 may be used in combination with any one or more of the preceding aspects.

In accordance with a thirtieth aspect of the present disclosure, any of the structure and functionality illustrated and described in connection with FIG. 5 may be used in combination with any one or more of the preceding aspects.

In accordance with a thirty-first aspect of the present disclosure, any of the structure and functionality illustrated and described in connection with FIG. 6 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A blood access device comprising:
a conductive needle in electrical communication with a first lead and configured to pierce a patient's skin and gain access to a blood vessel;
an insulative housing supporting a fluid communication junction between the needle and a flexible tube; and
a conductor in electrical communication with a second lead and having a first end connected to the insulative housing and a second end extending from the insulative housing in a direction coextensive with the needle such that (i) when the needle has gained access to the blood vessel, the conductor is electrically insulated from the conductive needle and (ii) if the needle is pulled so as to interrupt access with the blood vessel, the conductive needle and the conductor come into contact with each other, and wherein the conductive needle is radially offset from the longitudinal axis of the conductor for both (i) and (ii).

2. The blood access device of claim 1, wherein a dialysis machine can interface electrically with the first and second leads to ensure that the needle has access to the blood vessel while performing a dialysis machine function.

3. The blood access device of claim 1, which includes a voltage source and a signal emitter in electrical communication with the first and second leads.

4. The blood access device of claim 3, which includes a signal receiver connected operably to a dialysis machine, the signal receiver receiving a signal or a change in signal from the signal emitter when the needle access to the blood vessel has been interrupted.

5. The blood access device of claim 1, which includes an alarming device in electrical communication with the first and second leads, the alarming device providing an alarm when the conductive needle comes into contact with the conductor.

6. The blood access device of claim 5, which includes a voltage source in electrical communication with the first and second leads.

7. The blood access device of claim 1, wherein the conductor is moveably connected to the insulative housing, the second end adjacent to the insulative housing when the conductor is in an inactivated position, the second end extending from the insulative housing adjacent to a tip of the needle when the conductor is in an activated position.

8. The blood access device of claim 1, wherein the conductor is slideably or rotatably connected to the insulative housing.

9. The blood access device of claim 1, the conductor including a first electrode, the insulative housing including a second electrode, the first and second electrodes coming into contact with each other when the conductor is in the activated position.

10. The blood access device of claim 9, wherein a dialysis machine can interface electrically with the first and second leads to ensure that the needle has gained access to the blood vessel before performing a dialysis machine function.

11. The blood access device of claim 9, which includes third and fourth leads extending from the first and second electrodes, respectively, a voltage source and a signal emitter in electrical communication with the third and fourth leads.

12. The blood access device of claim 11, which includes a signal receiver connected operably to a dialysis machine, the signal receiver receiving a signal or a change in signal from the signal emitter when the needle has gained access to the blood vessel, the signal needed for the dialysis machine to perform a function.

13. The blood access device of claim 1, wherein the conductor is at least one of: (i) biased to contact the conductive needle; and (ii) wide enough to account for a misalignment between the conductor and the conductive needle.

14. The blood access device of claim 7, which is configured to automatically move the conductor to the activated position upon the needle gaining access to the blood vessel.

15. The blood access device of claim 7, wherein the insulative housing includes first and second mounting flanges that rotate into a position to be secured to the patient's arm, and which includes a mechanism that uses the rotation of at least one of the first and second mounting flanges to automatically move the conductor to the activated position.

16. A blood access device comprising:
a conductive needle configured to gain access to a patient's blood vessel;
first and second leads, the first lead in electrical communication with the conductive needle; and
a conductor in electrical communication with the second lead, the conductor extending in a same direction as the needle and moveable from an unactivated position to an activated position, wherein the conductor in the activated position is located such that (i) when the needle has gained access to the blood vessel, the conductive needle is electrically insulated from the conductor and (ii) if the needle is pulled so as to interrupt access with the blood vessel, the conductive needle and the conductor come into contact with each other.

17. The blood access device of claim 16, wherein the first and second leads extend to one of: (i) a dialysis machine and (ii) an alarming device.

18. The blood access device of claim 16, wherein the conductor is configured to be mechanically moved from the unactivated position to the activated position.

19. The blood access device of claim 16, which is configured to make an electrical contact upon reaching the activated position, the electrical contact usable to enable a dialysis machine function.

20. The blood access device of claim 16, wherein the conductor is connected to a housing, the housing constructed and arranged to aid the needle in gaining access to the patient's blood vessel.

21. The blood access device of claim 16, wherein the conductor is made of a superelastic material preset so that the conductor extends in a same direction as the needle.

\* \* \* \* \*